United States Patent
Brieden et al.

(10) Patent No.: US 7,358,073 B2
(45) Date of Patent: Apr. 15, 2008

(54) PROCESS FOR THE PREPARATION OF AMINOALCOHOL DERIVATIVES AND THEIR FURTHER CONVERSION TO (1R, 4S)-4(2-AMINO-6-CHLORO-5-FORMAMIDO-4-PYRIMIDINYL)-AMINO-2-CYCLOPENTENYL-1-METHANOL

(75) Inventors: Walter Brieden, Brig (CH); Josef Schroer, Susten (CH); Christine Bernegger-Egli, Munster (CH); Eva Maria Urban, Visp (CH); Michael Petersen, Visp (CH); Jean-Paul Roduit, Grone (CH); Katja Berchtold, Baltschieder (CH); Holger Breitbach, Baltschieder (CH)

(73) Assignee: Lonza AG, Basel (CH)

( * ) Notice: Subject to any disclaimer, the term of this patent is extended or adjusted under 35 U.S.C. 154(b) by 151 days.

(21) Appl. No.: 11/421,266

(22) Filed: May 31, 2006

(65) Prior Publication Data

US 2006/0211862 A1    Sep. 21, 2006

Related U.S. Application Data

(62) Division of application No. 10/695,930, filed on Oct. 29, 2003, which is a division of application No. 09/198,427, filed on Nov. 24, 1998, now Pat. No. 6,723,868.

(30) Foreign Application Priority Data

| Nov. 27, 1997 | (CH) | ................................ | 2739/97 |
| Dec. 3, 1997 | (CH) | ................................ | 2781/97 |
| Jan. 21, 1998 | (CH) | ................................ | 0133/98 |
| Mar. 27, 1998 | (CH) | ................................ | 0723/98 |
| Oct. 7, 1998 | (EP) | ................................ | 98118895 |

(51) Int. Cl.
*C12N 9/00*    (2006.01)

(52) U.S. Cl. .................................... 435/183

(58) Field of Classification Search ............... None
See application file for complete search history.

(56) References Cited

U.S. PATENT DOCUMENTS

| 2,534,533 A | 12/1950 | Schlesinger |
| 4,138,562 A | 2/1979 | Vince |
| 4,916,224 A | 4/1990 | Vince |
| 5,034,394 A | 7/1991 | Daluge |
| 5,049,671 A | 9/1991 | Daluge |
| 5,087,697 A | 2/1992 | Daluge |
| 5,200,527 A | 4/1993 | Griffiths et al. |
| 5,206,435 A | 4/1993 | Daluge |
| 5,294,423 A | 3/1994 | Lorthioir et al. |
| 5,847,201 A | 12/1998 | Wieczorek |
| 5,917,042 A | 6/1999 | Daluge |
| 6,156,893 A | 12/2000 | Bernegger |

FOREIGN PATENT DOCUMENTS

| DE | 947702 | 8/1956 |
| EP | 508352 | 4/1992 |
| EP | 512895 | 4/1993 |
| WO | WO-9317020 | 9/1993 |
| WO | WO-9521161 | 8/1995 |
| WO | WO-9919327 | 4/1999 |

OTHER PUBLICATIONS

Katagiri et al., Chem. Pharm. Bull., 39(5), 1112-1122, 1991.
Campbell et al., J. Org. Chem. 1995, 60, 4602-2616.
Taylor S. J. et al., Tetrahetron: Asymmetry vol. 4, No. 6, 1993, 1117-1128.
Park K.H. & Rappoport H., J. Org. Chem. 1994, 59, 394-399.
Martinez et al. (J. Org. Chem. 1996, 61, 7963-7966).
Katagiri et al., (Tetrahedron Letters, 1989, 30, 1645-1658).
Malpass & Tweedle, J. Chem. Soc., Perkin Trans 1, 1977, 874-884).
H.C. Brown et al., Inorg. Chec. 20, 1981, 4456-4457.
Balkenhohl et al., 1997, J. Prakt. Chem. 338, 381-384.
K. Farber, Biotransformation In Organic Chemistry, 2nd ed., Berlin 1995, 270-305.

*Primary Examiner*—Michael Meller
(74) *Attorney, Agent, or Firm*—Darby & Darby

(57) ABSTRACT

The invention relates to a novel process for the preparation of an aminoalcohol of the formula

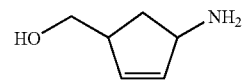

racemically or optically active, starting from 2-azabicyclo [2.2.1]hept-5-en-3-one, its further conversion to give the corresponding acyl derivative and its further conversion to (1S,4R)- or (1R,4S)-4-(2-amino-6-chloro-9-H-purine-9-yl)-2-cyclopentenyl-1-methanol of the formulae

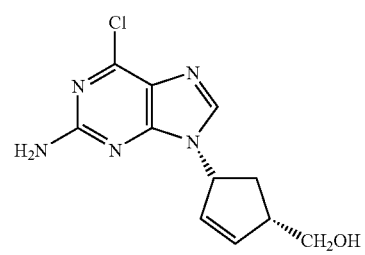

XI

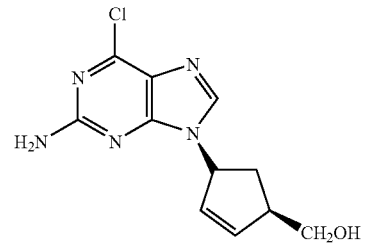

XII

In the latter synthesis, the aminoalcohol is converted into the corresponding D- or L-tartrate, which is then reacted with N-(2-amino-4,6-dichloropyrimidin-5-yl) formamide of the formula

XIII

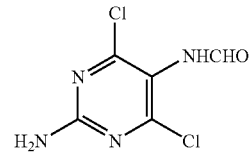

to give (1S,4R)- or (1R,4S)-4-[(2-amino-6-chloro-5-formamido-4-pyrimidinyl)amino]-2-cyclopentenyl-1-methanol of the formulae
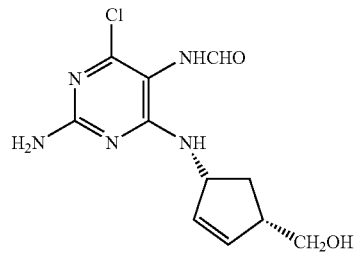
XIV
-continued
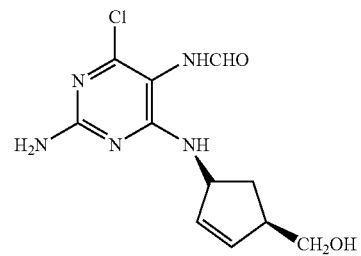
XV
and then cyclized to give the end compounds.
2 Claims, No Drawings

PROCESS FOR THE PREPARATION OF AMINOALCOHOL DERIVATIVES AND THEIR FURTHER CONVERSION TO (1R, 4S)-4(2-AMINO-6-CHLORO-5-FORMAMIDO-4-PYRIMIDINYL)-AMINO-2-CYCLOPENTENYL-1-METHANOL

This application is a divisional of U.S. Ser. No. 10/695,930, filed Oct. 29, 2003, which is a divisional of U.S. Ser. No. 09/198,427, filed Nov. 24, 1998 now U.S. Pat. No. 6,723,868, and claims the benefit of (1) Swiss Patent Application No. 2739/97, filed Nov. 27, 1997, (2) Swiss Patent Application No. 2781/97, filed Dec. 3, 1997, (3) Swiss Patent Application No. 0133/98, filed Jan. 21, 1998, (4) Swiss Patent Application No. 0723/98, filed Mar. 27, 1998, and (5) European Patent Application No. 98118895.6, filed Oct. 7, 1998, all of which are hereby incorporated by reference.

The present invention relates to a novel process for the preparation of (1R, 4S)- or (1S, 4R)-1-amino-4-(hydroxymethyl)-2-cyclopentene of the formulae

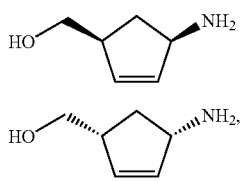

or salts thereof, or the D- or L-hydrogentartrates thereof and also their further conversion to give (1S, 4R)-or (1R, 4S)-4-(2-amino-6-chloro-9-H-purine-9-yl)-2-cyclopentene. (1R, 4S)-1-Amino-4-(hydroxymethyl)-2-cyclopentene of the formula IV is an important intermediate for the preparation of carbocyclic nucleosides such as, for example, Carbovir® (Campbell et al., J. Org. Chem. 1995, 60, 4602-4616).

A process for the preparation of (1R, 4S)-1-amino-4-(hydroxymethyl)-2-cyclopentene is described, for example, by Campbell et al. (ibid) and by Park K. H. & Rapoport H. (J. Org. Chem. 1994, 59, 394-399).

In this process, the starting material is either D-glucono-δ-lactone or D-serine, approximately 15 synthesis stages being required to form (1R, 4S)-N-tert-butoxycarbonyl-4-hydroxymethyl-2-cyclopentene, and the protecting group is removed to give (1R, 4S)-1-amino-4-(hydroxymethyl)-2-cyclopentene.

Both these processes are costly, complex and not practicable industrially. WO 93/17020 describes a process for the preparation of (1R, 4S)-1-amino-4-(hydroxymethyl)-2-cyclopentene, in which (1R, 4S)-4-amino-2-cyclopentene-1-carboxylic acid is reduced to the desired product using lithium aluminium hydride.

Disadvantages of this process are firstly that the double bond of the cyclopentene ring is also reduced, the poor handling properties of lithium aluminium hydride and secondly that it is too costly.

Taylor S. J. et al. (Tetrahetron: Asymmetry Vol. 4, No. 6, 1993, 1117-1128) describe a process for the preparation of (1R, 4S)-1-amino-4-(hydroxymethyl)-2-cyclopentene starting from (±)-2-azabicyclo[2.2.1]hept-5-en-3-one as starting material. In this process, the starting material is converted, using microorganisms of the species *Pseudomonas solanacearum* or *Pseudomonas fluorescens*, into (1R, 4S)-2-azabicyclo[2.2.1]hept-5-en-3-one, which is then reacted with di-tert-butyl dicarbonate to give (1R, 4S)-N-tert-butoxycarbonyl-2-azabicyclo[2.2.1]hept-5-en-3-one, and the latter is reduced using sodium borohydride and trifluoroacetic acid to give the desired product.

This process is far too costly.

In addition, Martinez et al. (J. Org. Chem. 1996, 61, 7963-7966) describe a 10-stage synthesis of (1R, 4S)-1-amino-4-(hydroxymethyl)-2-cyclopentene starting from diethyl dialkylmalonate. This process too has the disadvantage that it is complex and not practicable industrially.

It is also known that N-substituted (±)-2-azabicyclo-[2.2.1]hept-5-en-3-ones, which carry an electron-withdrawing substituent, can be reduced to the corresponding N-substituted aminoalcohols using a metal hydride (Katagiri et al., Tetrahedron Letters, 1989, 30, 1645-1648; Taylor et al., ibid).

In contrast to this, it is known that unsubstituted (±)-2-azabicyclo[2.2.1]hept-5-en-3-one of the formula

is reduced with lithium aluminium hydride to give (±)-2-azabicyclo[2.2.2]octene (Malpass & Tweedle, J. Chem. Soc., Perkin Trans 1, 1977, 874-884), and that the direct reduction of (±)-2-azabicyclo[2.2.2]hept-5-en-3-one to give the corresponding aminoalcohol has to date been impossible (Katagiri et al., ibid; Taylor et al., ibid)

It is also known to resolve racemic 1-amino-4-(hydroxymethyl)-2-cyclopentene using (−)-dibenzoyltartaric acid (U.S. Pat. No. 5,034,394). On the one hand, this reaction has the disadvantage that (−)-dibenzoyltartaric acid is expensive, and, on the other hand, that the separation must take place in the presence of an exactly defined mixture of acetonitrile and ethanol. This solvent mixture cannot be removed and must be fed to the combustion.

The object of the present invention was to provide a simple, economical and cost-effective process for the preparation of a (1R, 4S)-1-amino-4-(hydroxymethyl)-2-cyclopentene.

Surprisingly, it has now been found that when (±)-2-azabicyclo[2.2.1]hept-5-en-3-one of the formula

in the form of the racemate or one of its optically active isomers, is reduced with a metal hydride, the aminoalcohol of the formula

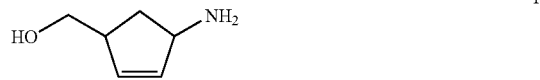

in the form of the racemate or one of its optically active isomers is obtained in a simple manner.

As the person skilled in the art is aware, the aminoalcohol of the formula I can be converted using an acid into the corresponding salts, such as, for example, into hydrohalide salts. Suitable hydrohalide salts are hydrobromides and hydrochlorides.

The starting material, the (±)-2-azabicyclo-[2.2.1]hept-5-en-3-one can be prepared according to EP-A 0 508 352.

Metal hydrides which may be used are alkali metal or alkaline earth metal hydrides and also binary or complex metal hydrides of the boron or aluminium group, such as alkali metal and alkaline earth metal borohydrides, alkali metal and alkaline earth metal aluminium hydrides. Suitable alkali metal or alkaline earth metal hydrides are LiH, NaH, KH, BeH$_2$, MgH$_2$ or CaH$_2$.

Binary alkali metal or alkaline earth metal borohydrides which may be used are NaBH4, LiBH$_4$, KBH$_4$, NaAlH$_4$, LiAlH$_4$, KAlH$_4$, Mg(BH$_4$)$_2$, Ca(BH$_4$)$_2$, Mg(AlH$_4$)$_2$ and Ca(AlH$_4$)$_2$. Complex metal hydrides of the boron or aluminium group may have the general formula M$^1$M$^2$H$_n$L$_m$, in which n is an integer from 1 to 4, and m is an integer from 4 to 4 minus the corresponding number n, M$^1$ is an alkali metal atom, M$^2$ is boron or aluminium, and L is C$_{1-4}$-alkyl, C$_{1-4}$-alkenyl, C$_{1-4}$-alkoxy, CN or an amine, or the complex metal hydrides may have the general formula M$^2$H$_O$L$_p$, in which M$^2$ is as defined above and O is an integer from 0 to 3, and p is an integer from 3 to 3 minus the corresponding number p. Possible M$^1$M$^2$H$_n$L$_m$ compounds are LiBH (C$_2$H$_5$)$_3$, LiBH$_x$(OCH$_3$)$_{4-x}$, LiAlH(OC(CH$_3$)$_3$)$_3$, NaAlH$_2$(OC$_2$H$_4$OCH$_3$)$_2$, NaAlH$_2$(C$_2$H$_5$)$_2$ or NaBH$_3$CN. Preferably, the reduction is carried out using a metal borohydride. As an expert in the art is aware, the metal hydrides mentioned such as, for example, LiBH$_4$, can also be produced "in situ". Common preparation methods for LiBH$_4$ are, for example, the reaction of an alkali metal borohydride with a lithium halide (H. C. Brown et al., Inorg. Chem. 20, 1981, 4456-4457), the reaction of LiH with B$_2$O$_3$ in the presence of hydrogen and a hydrogenation catalyst (EP-A 0 512 895), the reaction of LiH with (H$_5$C$_2$)OBF$_3$ (DE-A 94 77 02) and that of LiH with B(OCH$_3$)$_3$ (U.S. Pat. No. 2,534,533).

The metal hydrides are expediently used in a molar ratio of from 1 to 5 per mole of (±)-2-azabicyclo-[2.2.1]hept-5-en-3-one.

The metal hydrides, in particular NaBH$_4$, are preferably used with lithium salt additives. Lithium salts which may be used are LiCl, LiF, LiBr, LiI, Li$_2$SO$_4$, LiHSO$_4$, Li$_2$CO$_3$, Li(OCH$_3$) and LiCO$_3$.

The reduction is expediently carried out in an inert-gas atmosphere, such as, for example, in an argon or nitrogen atmosphere.

The reduction can be carried out at a temperature of from −20 to 200° C., preferably at a temperature of from 60 to 150° C.

Suitable solvents are aprotic or protic organic solvents. Suitable aprotic organic solvents may be ethers or glycol ethers, such as, for example, diethyl ether, dibutyl ether, ethyl methyl ether, diisopropyl ether, tert-butyl methyl ether, anisole, dioxane, tetrahydrofuran, monoglyme, diglyme and formaldehyde dimethyl-acetal. Suitable protic organic solvents are C$_{1-6}$-alcohols, such as methanol, ethanol, propanol, isopropanol, butanol, tert-butanol, pentanol, tert-amyl alcohol or hexanol and also mixtures of these with water. Suitable protic organic solvents are also mixtures of one of said ethers, glycol ether with water or with one of said alcohols, such as a mixture of a C$_{1-6}$-alcohol with an ether or glycol ether, in particular a mixture of methanol, ethanol or water with diethyl ether, tetrahydrofuran, dioxane, glyme or diglyme. The solvent used is preferably a protic organic one, such as a mixture of a C$_{1-6}$-alcohol or water with an ether or glycol ether.

In a preferred embodiment, the reduction is carried out in the presence of an additive, such as in the presence of water or of a lower aliphatic alcohol. The lower aliphatic alcohol may be methanol, ethanol, methoxyethanol, n-propanol, isopropanol, isobutanol, tert-butanol, n-butanol, diols such as butanediol, and triols such as glycerol. In particular, the lower aliphatic alcohol is methanol or ethanol. Here, the lower aliphatic alcohol is expediently used in a molar ratio of from 2 to 15 per mol of (±)-2-azabicyclo[2.2.1]hept-5-en-3-one.

If the reaction is carried out in the presence of said alcohol, the corresponding amino acid ester can be formed in situ (intermediate). I.e. if the starting material used is (±)-2-azabicyclo[2.2.1]hept-5-en-3-one, according to the invention the corresponding (±)-amino acid ester can be formed. If the starting material used is (−)-2-azabicyclo [2.2.1]hept-5-en-3-one, according to the invention the (−)-amino acid ester can correspondingly be formed as intermediate.

Surprisingly, it has also been found that when a cyclopentene derivative of the general formula

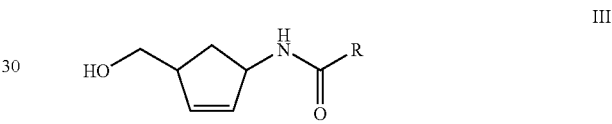

III in the form of the racemate or one of its optically active isomers, in which R is C$_{1-4}$-alkyl, C$_{1-4}$-alkoxy, aryl or aryloxy, is hydrolyzed with an alkali metal hydroxide, the aminoalcohol of the formula

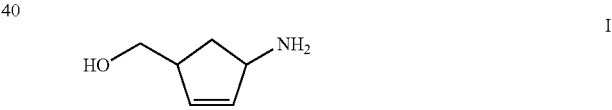

I in the form of the racemate or one of its optically active isomers is obtained in a simple manner.

C$_{1-4}$-Alkyl can be substituted or unsubstituted. In the text below substituted C$_{1-4}$-alkyl is taken to mean C$_{1-4}$-alkyl substituted by a halogen atom. The halogen atom may be F, Cl, Br or I. Examples of C$_{1-4}$-alkyl are methyl, ethyl, propyl, butyl, isobutyl, tert-butyl, isopropyl, chloromethyl, bromomethyl, dichloromethyl and dibromomethyl. The C$_{1-4}$-alkyl is preferably methyl, ethyl, propyl, butyl, isobutyl or chloromethyl.

The C$_{1-4}$-alkoxy used may be, for example, methoxy, ethoxy, propoxy or butoxy. The aryl used can be, for example, phenyl or benzyl, substituted or unsubstituted. The aryloxy used can be, for example, benzyloxy or phenoxy, substituted or unsubstituted.

The alkali metal hydroxide used may be sodium or potassium hydroxide.

For this process variant, the cyclopentene derivative of the general formula III is preferably prepared by reduction of the corresponding acyl-2-azabicyclo[2.2.1]hept-5-en-3-one of the general formula

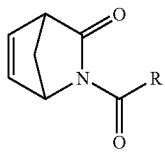

in the form of the racemate or one of its optically active isomers, in which R is as defined above, using one of the metal hydrides already mentioned in an anhydrous solvent.

The anhydrous solvent may be protic or aprotic organic solvents, in particular an anhydrous protic organic solvent such as a tertiary alcohol. The tertiary alcohol may be tert-butyl alcohol or tert-amyl alcohol.

As already mentioned above, this reduction is also preferably carried out in the presence of an addition, such as in the presence of a lower aliphatic alcohol such as methanol, in particular in the presence of 2 mol of methanol per mole of acyl-2-azabicyclo-[2.2.1]hept-5-en-3-one (formula IV).

The reaction is expediently carried out at a temperature of from 0 to 50° C., preferably from 15 to 30° C.

The racemic aminoalcohol of the formula I is then converted according to the invention either by chemical means using an optically active tartaric acid or by biotechnological means using a hydrolase in the presence of an acylating agent to give (1R, 4S)- or (1S, 4R)-1-amino-4-(hydroxymethyl)-2-cyclopentene of the formula

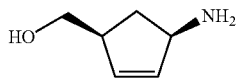

or salts thereof and/or to give (1S, 4R)- or (1R, 4S)-1-amino-4-(hydroxymethyl)-2-cyclopentene derivative of the general formulae

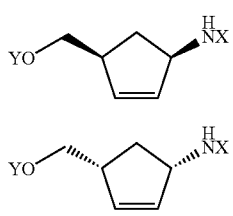

or salts thereof, in which X and Y are identical or different and are an acyl group or H, with the exception of X=Y=H.

The hydrolases used may be lipases, proteases, amidases or esterases, lipases being expediently used.

In the text below, salts are taken to mean hydrohalide salts such as hydrochlorides, hydrobromides or tartrates.

As the person skilled in the art is aware, hydrolase-catalyzed acylations in which optically active compounds are formed are carried out in the presence of a suitable acylating agent (Balkenhohl et al., 1997, J. Prakt. Chem. 339, 381-384; K. Faber, "Biotransformation in Organic Chemistry", 2nd ed., Berlin 1995, 270-305). Suitable acylating agents are generally carboxylic acid derivatives such as carboxamides, carboxylic anhydrides or carboxylic esters. The carboxylic esters may, for example, be alkoxycarboxylic esters, such as ethyl methoxyacetate and isopropyl methoxyacetate, $C_{1-6}$-carboxylic esters, such as butyl acetate, ethyl butyrate and ethyl hexanoate, glyceryl esters, such as tributyrin (glyceryl tributyrate), glycol esters, such as glycol dibutyrate and diethyl diglycolate, dicarboxylic esters, such as diethyl fumarate and malonate, cyanocarboxylic esters, such as ethyl cyanoacetate, or cyclic esters, such as, for example, 6-caprolactone.

Accordingly, the acyl group in the formulae VII and VIII corresponds to the acid component of the carboxylic acid derivative used.

The lipases used may be standard commercial lipases, such as, for example: Novo lipase SP523 from *Aspergillus oryzae* (Novozym 398), Novo lipase SP524 from *Aspergillus oryzae* (lipase=Palatase 20000 L from Novo) Novo lipase SP525 from *Candida antarctica* (lipase B Novozym 435, immobilized), Novo lipase SP526 from *Candida antarctica* (lipase A=Novozym 735, immobilized), lipase kits from Fluka (1 & 2), Amano P lipase, lipase from *Pseudomonas* sp., lipase from *Candida cylindracea*, lipase from *Candida lypolytica*, lipase from *Mucor miehei*, lipase from *Aspergillus niger*, lipase from *Bacillus thermocatenulatus*, lipase from *Candida antarctica*, lipase AH (Amano; immobilized), lipase P (Nagase), lipase AY from *Candida rugosa*, lipase G (Amano 50), lipase F (Amano F-AP15), lipase PS (Amano), lipase AH (Amano), lipase D (Amano), lipase AK from *Pseudomonas fluorescens*, lipase PS from *Pseudomonas cepacia*, newlase I from *Rhizopus niveus*, lipase PS-CI (immobilized lipase from *Pseudomonas cepacia*). These lipases may, as the person skilled in the art is aware, be used as cell-free enzyme extracts or else in the corresponding microorganism cell.

The proteases may also be commercially available, such as, for example, serine proteases such as subtilisins. The subtilisin may be savinase from *Bacillus* sp., alcalase, subtilisin from *Bacillus licheniformis* and also proteases from *Aspergillus, Rhizopus, Streptomyces* or *Bacillus* sp.

The biotechnological racemate resolution is expediently carried out at a temperature of from 10 to 80° C. and at a pH of from 4 to 9.

The biotechnological racemate resolution is expediently carried out in a protic or aprotic organic solvent. Suitable aprotic organic solvents are ethers such as tert-butyl methyl ether, diisopropyl ether, dibutyl ether, dioxane and tetrahydrofuran, aliphatic hydrocarbons such as hexane, organic bases such as pyridine, and carboxylic esters such as ethyl acetate, and suitable protic organic solvents are the $C_{1-6}$-alcohols already described, such as, for example, pentanol.

The (1S, 4R)- or (1R, 4S)-1-amino-4-(hydroxymethyl)-2-cyclopentene derivatives of the general formulae VII and VIII formed in accordance with the invention during the biotechnological racemate resolution are, depending on the desired target compound (aminoalcohol of the formula V or VI), hydrolyzed by chemical means to give the aminoalcohol of the formula V or VI. The chemical hydrolysis is expediently carried out in an aqueous basic solution or using a basic ion exchanger. The aqueous basic solution is preferably, as for the hydrolysis of the cyclopentene derivatives of the general formula III described above, an alkali metal hydroxide. The basic ion exchangers can, for example, be Dowex 1×8(OH⁻) and Duolite A147.

The chemical racemate resolution is carried out using an optically active tartaric acid such as using D-(−)-tartaric acid or L-(+)-tartaric acid.

The racemate resolution with D-(−)-tartaric acid is expediently carried out by firstly reacting the racemic 1-amino-4-(hydroxymethyl)-2-cyclopentene with the D-(−)-tartaric acid in the presence of a lower aliphatic alcohol.

Suitable lower aliphatic alcohols are the same as those described above. Preference is given to using methanol. The reaction which leads to formation of the salt is usually carried out at temperature between 20° C. and the reflux temperature of the solvent, preferably at the reflux temperature.

If desired, the 1-amino-4-(hydroxymethyl)-2-cyclopentene D-tartrate formed during the reaction can be further purified by recrystallization from a lower aliphatic alcohol such as methanol.

The racemate resolution with L-(+)-tartaric acid is expediently carried out as that with D-(−)-tartaric acid. I.e. the racemate resolution with L-(+)-tartaric acid is likewise carried out in the presence of a lower aliphatic alcohol and at a temperature between 20° C. and the reflux temperature of the solvent, preferably at the reflux temperature. After cooling, the (1S, 4R)-1-amino-4-(hydroxymethyl)-2-cyclopentene L-hydrogentartrate crystallizes out.

The (1R, 4S)-1-amino-4-(hydroxymethyl)-2-cyclopentene L-hydrogentartrate is present, in particular, in dissolved form in the mother liquor.

Isolation, further purification (liberation) and conversion to the corresponding salt of (1R, 4S)- or (1S, 4R)-1-amino-4-(hydroxymethyl)-2-cyclopentene takes place with a base and subsequent acid treatment. Suitable bases are alkali metal alkoxides, alkali metal or alkaline earth metal carbonates, or alkali metal or alkaline earth metal hydroxides. The alkali metal alkoxides may be sodium or potassium alkoxides. The alkali metal carbonate may be potassium or sodium carbonate, potassium or sodium hydrogencarbonate, and the alkaline earth metal carbonate may be magnesium or calcium carbonate. The alkali metal hydroxide may be sodium or potassium hydroxide, and the alkaline earth metal hydroxide may be calcium hydroxide. Conversion to the corresponding salt usually takes place with a mineral acid such as with sulphuric acid, hydrochloric acid or phosphoric acid, preferably with hydrochloric acid.

(1R, 4S)- or (1S, 4R)-1-amino-4-(hydroxymethyl)-2-cyclopentene D-hydrogentartrate and (1R, 4S)- or (1S, 4R)-1-amino-4-(hydroxymethyl)-2-cyclopentene L-hydrogen-tartrate are compounds unknown in the literature and are likewise provided by the invention.

Preference is given to carrying out the chemical racemate resolution with D-(+)-tartaric acid due to the higher performance, technical facility and more efficient racemate resolution.

As for the racemic aminoalcohol, it is of course also possible to react the optically active (1R, 4S)- or (1S, 4R)-1-amino-4-(hydroxymethyl)-2-cyclopentenes with D-(−)- or L-(+)-tartaric acid to give the corresponding tartrates.

A further constituent of the present invention is the further conversion, the acylation, of the (1R, 4S)- or (1S, 4R)-1-amino-4-(hydroxymethyl)-2-cyclopentenes to give the (1R, 4S)-1-amino-4-(hydroxymethyl)-2-cyclopentene derivative of the general formula

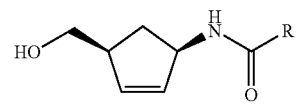

IX

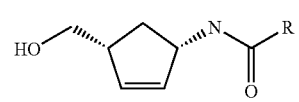

X

Here, the substituent R is as defined in the cyclopenten derivative of the general formula III.

The acylation can be carried out using a carbonyl halide of the general formula

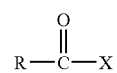

XVI in which X is a halogen atom, and R is as defined above, or using a carboxylic anhydride of the general formula

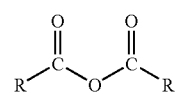

XVII in which R is as defined above.

The halogen atom X may be F, Cl, Br or I. Preference is given to Cl or F.

Examples of carbonyl halides are: acetyl chloride, chloroacetyl chloride, butyryl chloride, isobutyryl chloride, phenylacetyl chloride, benzyl chloroformate, propionyl chloride, benzoyl chloride, alkyl chloroformate or tert-butyloxycarbonyl fluoride.

Examples of carboxylic anhydrides are: tert-butoxycarbonyl anhydride, butyric anhydride, acetic anhydride or propionic anhydride. The acylation is preferably carried out using a carboxylic anhydride, in particular using tert-butoxycarbonyl anhydride.

The acylation can be carried out without solvent or using an aprotic organic solvent. The acylation is expediently carried out in an aprotic organic solvent. Suitable aprotic organic solvents are, for example, pyridine, acetonitrile, dimethylformamide, diisopropyl ether, tetrahydrofuran, toluene, methylene chloride, N-methylpyrrolidone, triethylamine, chloroform, ethyl acetate, acetic anhydride and mixtures thereof.

The acylation is expediently carried out at a temperature of from −20 to 100° C., preferably from 0 to 80° C.

The further conversion according to the invention of (1R, 4S)- or (1S, 4R)-1-amino-4-(hydroxymethyl)-2-cyclopentene D- or L-hydrogentartrate to (1S, 4R)- or (1R, 4S)-4-(2-amino-6-chloro-9-H-purine-9-yl)-2-cyclopentenyl-1-methanol, or a salt thereof, of the formulae

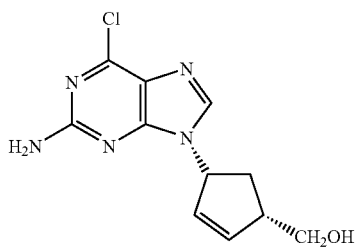

XI

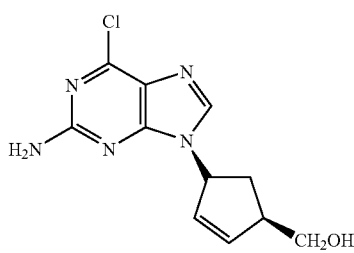

XII is carried out by reacting (1R, 4S)- or (1S, 4R)-1-amino-4-(hydroxymethyl)-2-cyclopentene D- or L-hydrogentartrate with N-(2-amino-4,6-dichloropyrimidin-5-yl)formamide of the formula

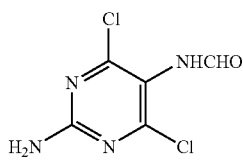

XIII to give (1S, 4R)- or (1R, 4S)-4-[(2-amino-6-chloro-5-formamido-4-pyrimidinyl) amino]-2-cyclopentenyl-1-methanol of the formulae

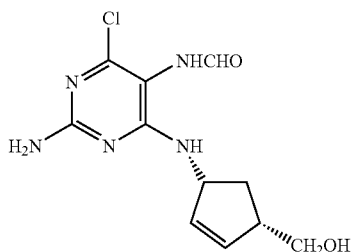

XIV

XV and then cyclizing the latter in a known manner to give the compounds according to formula VIII and IX.

N-(2-Amino-4,6-dichloropyrimidin-5-yl)formamide can be prepared according to WO 95/21 161.

The reaction is expediently carried out in the presence of a base. Suitable bases are the same as those previously described for liberating (1R, 4S)- or (1S, 4R)-1-amino-4-(hydroxymethyl)-2-cyclopentenes from the corresponding tartrate.

The reaction is expediently carried out in a protic solvent. The protic solvent may be lower aliphatic alcohols such as methanol, ethanol, propanol, isopropanol, butanol or isobutanol.

The (1S, 4R)- or (1R, 4S)-4-[(2-amino-6-chloro-5-formamido-4-pyrimidinyl)amino]-2-cyclopentenyl-1-methanol of the formula XI or XII is then cyclized in a known manner according to WO 95/21 161 to give the end product according to Formula VIII or IX.

The cyclization is usually carried out dissolved in trialkyl orthoformate in the presence of a concentrated aqueous acid. The trialkyl orthoformates used may be, for example, trimethyl or triethyl orthoformate.

The aqueous acid may be, for example, hydrogen fluoride, sulphuric acid or methanesulphonic acid.

A further constituent of the invention is the overall process for the preparation of (1S, 4R)-4-(2-amino-6-chloro-9-H-purine-9-yl)-2-cyclopentenyl-1-methanol, or salts thereof, of the formula XII starting from (−)-2-azabicyclo[2.2.1]hept-5-en-3-one or (−)-acyl-2-azabicyclo[2.2.1]hept-5-en-3-one of the formulae

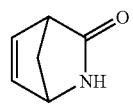

II

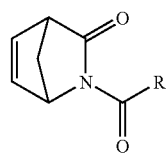

IV in which R is as defined above, by reduction with a metal hydride to give an aminoalcohol of the formula

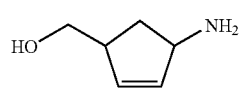

I or to give a cyclopentene derivative of the general formula

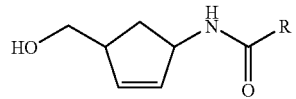

III in which R is as defined above, which are then converted into the corresponding hydrohalide salts, and then reacted with N-(2-amino-4,6-dichloropyrimidin-5-yl)-formamide of the formula

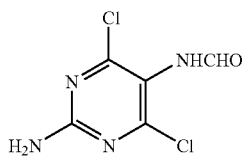

to give (1S, 4R)-4-[(2-amino-6-chloro-5-formamido-4-pyrimidinyl)amino]-2-cyclopentenyl-1-methanol of the formula

XV

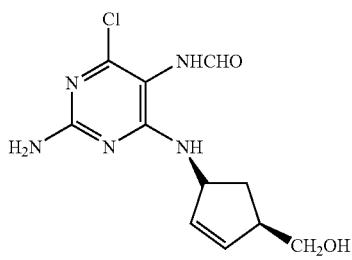

and then the latter is cyclized in a known manner to give the compound of the formula

XII

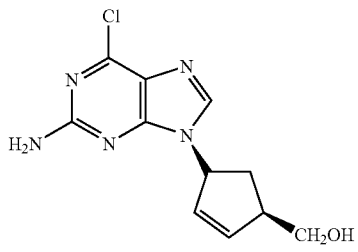

This process variant has the advantage that the hydrohalide salts formed therein may be used as a crude mixture in the preparation of the product of the formula XII.

EXAMPLES

Example 1

Reduction of acyl- or Unsubstituted-2-azabicyclo[2.2.1]-hept-5-en-3-one 1.1. Preparation of (±)-acetyl-1-amino-4-(hydroxymethyl)-2-cyclopentene in an Anhydrous Protic Organic Solvent Using Sodium Borohydride 280 g of 2-methyl-2-butanol (amyl alcohol) and 15.2 g of sodium borohydride (0.4 mol) were charged into a sulphonation flask at 20° C. A mixture of 907 g of (±)-acetyl-2-azabicyclo[2.2.1]hept-5-en-3-one (0.6 mol) and 37.5 g of methanol (2 equivalents based on (±)-acetyl-2-azabicyclo [2.2.1]hept-5-en-3-one was metered into this suspension over the course of 2 h at 20° C. The reaction mixture was then stirred for a further 3 h at 20° C. The solvent was distilled as far as possible (40° C.). Boron was removed by adding 280 g of methanol and 27.2 g of formic acid, warming the mixture to 25-30° C. and distilling off the methyl borate/methanol azeotrope at this temperature (130 to 80 mbar). The precipitated sodium formate was filtered off, and the filtrate was reduced by evaporation to give 93.4 g of crude product as a clear viscous oil; crude yield: about 84-85%.

1.2. Preparation of cis-1-amino-4-(hydroxymethyl)-2-cyclopentene

A suspension of (±)-2-azabicyclo[2.2.1]hept-5-en-3-one (10.00 g, 91.6 mmol) and lithium borohydride (4.00 g, 183.7 mmol) in dry dioxane (100 ml) was heated in an inert-gas atmosphere (argon) for 4 h at 110° C. below the reflux temperature. After this time, about 20-25% of the starting material had reacted to give the product (GC analysis with internal standard benzophenone after work-up of the reaction mixture; work-up: 0.05 ml of the reaction mixture were quenched with 0.1 ml of 1M HCl and immediately rendered basic using 0.2 ml of 1M NaOH).

The structural detection of the product was carried out by H-NMR, GC and GC-MS.

1.3. Preparation of (+)-1-amino-4-(hydroxymethyl)-2-cyclopentene

A 25 ml round-bottom flask was charged with 1.0 g (9.2 mmol) of (+)-2-azabicyclo[2.2.1]hept-5-en-3-one and 0.4 g (18.4 mmol) of lithium borohydride, under an inert-gas atmosphere, in 10 ml of dioxane, and the mixture was refluxed for 3 h at 110° C. Excess reducing agent was destroyed by adding about 5 ml of semi-concentrated HCl (adjusted to pH 3). The mixture was then immediately buffered by adding about 1 ml of saturated NaHCO$_3$ solution at pH 8. GC analysis indicated the formation of the product. The entire reaction mixture was then evaporated to dryness and purified by means of column chromatography (gradient: hexane/ethyl acetate/MeOH=1:1:1–>MeOH). In this way (+)-2-azabicyclo-[2.2.1]hept-5-en-3-one and the corresponding (+)-aminoalcohol were obtained.

1.4. Preparation of (−)-1-amino-4-(hydroxymethyl)-2-cyclopentene

A 25 ml round-bottom flask was charged with 1.0 g (9.2 mmol) of (−)-2-azabicyclo[2.2.1]hept-5-en-3-one and 0.4 g (18.4 mmol) of lithium borohydride, under an inert-gas atmosphere, in 10 ml of dioxane, and the mixture was refluxed for 3 h at 110° C. Excess reducing agent was destroyed by adding about 5 ml of semi-concentrated HCl (adjusted to pH 3). The mixture was then immediately buffered by adding about 1 ml of saturated NaHCO$_3$ solution at pH 8. GC analysis indicated the formation of the product in 18% yield (GC standard is benzophenone). The entire reaction mixture was then evaporated to dryness and purified by means of column chromatography (gradient: hexane/ ethyl acetate/MeOH=1:1:1–>MeOH). In this way, 0.43 g (43%) of (−)-2-azabicyclo[2.2.1]-hept-5-en-3-one was reisolated and 0.04 g (4%) of the corresponding (−)-aminoalcohol was obtained.

By HPLC, only the (−)-enantiomer of the aminoalcohol was detectable. The ee of the product is thus >98%.

1.5. Preparation of (±)-1-amino-4-(hydroxymethyl)-2-cyclopentene in an Alcohol

A 100 ml round-bottom flask fitted with magnetic stirrer was charged with 3.0 g (27.5 mmol) of (±)-2-azabicyclo [2.2.1]hept-5-en-3-one and 1.2 g (28.3 mmol) of lithium borohydride, under an inert-gas atmosphere, in 35 g of 2-butanol, and the mixture was stirred for 3 h at 60° C. GC analysis of a sample (work-up: 0.1 g sample rendered acidic using 0.2 ml of 1M HCl, then quickly rendered basic using 0.1 ml of saturated NaHCO$_3$) indicated the formation of the product in 12% yield after this time. (GC standard is benzophenone.)

1.6. Preparation of a (±)-1-amino-4-(hydroxymethyl)-2-cyclopentene in an Alcohol/Ether Mixture A 10 ml round-bottom flask was charged under at inert-gas atmosphere with 0.5 g (4.6 mmol) of (±)-2-azabicyclo[2.2.1]hept-5-en-3-one and 0.59 g (18.4 mmol) of methanol in 7.5 ml of dioxane (abs.). 0.21 g (9.2 mmol) of lithium borohydride were added, and the mixture was heated for 4 h at 60° C. The mixture was then cooled to 5° C. using an ice/waterbath, and about 10 ml of semi-concentrated HCl was carefully added to the reaction mixture (vigorous reaction, gas evolution), as a result of which a yellowish clear solution formed. This solution was analyzed directly by a quantitative ion-chromatographic method. It contained 0.60 mmol (13.1%) of (±)-2-azabicyclo[2.2.1]hept-5-en-3-one (determined as HCl salt of the corresponding amino acid, which is the acidic hydrolysis product of (±)-2-azabicyclo[2.2.1]hept-5-en-3-one) and 3.06 mmol of product, corresponding to a yield of 66.8%, aminoalcohol.

1.7. Preparation of (±)-1-amino-4-(hydroxymethyl)-2-cyclopentene in the Presence of Additives Such as Water or Various Alcohols A 10 ml round-bottom flask was charged with 0.50 g (4.66 mmol) of (+)-2-azabicyclo[2.2.1]hept-5-en-3-one and 0.30 g (13.7 mmol) of lithium borohydride in 7.5 ml of abs. dioxane, and the mixture was heated to 60° C.

At this temperature, over the course of 30 min, X mmol of alcohol Y was added dropwise using a syringe. The mixture is then stirred for 2 h at 60° C., cooled to about 20° C. and poured into about 10 ml of semi-concentrated HCl. The content was then determined directly using a quantitative ion-chromatographic method (cf. Table 1).

TABLE 1

| Example | Additive Y | X mmol | X equivalents | (±)-2-Azabicyclo-[2.2.1]-hept-5-en-3-one % yield | Aminoalcohol % yield |
|---|---|---|---|---|---|
| 1.7.1 | — | — | — | 15 | 52 |
| 1.7.2 | water | 17.1 | 1.25 | 23.3 | 67.5 |
| 1.7.3 | water | 34.3 | 2.5 | 32.3 | 58.3 |
| 1.7.4 | methanol | 34.3 | 2.5 | 4.5 | 83.1 |
| 1.7.5 | ethanol | 34.3 | 2.5 | 6.5 | 74.7 |
| 1.7.6 | isopropanol | 34.3 | 2.5 | 28.1 | 52.3 |

1.8. Preparation of (±)-1-amino-4-(hydroxymethyl)-2-cyclopentene with Various Amounts of Methanol Using the procedure of Example 1.7, the reaction was carried out in a variety of methanol concentrations. The results are given in Table 2.

TABLE 2

| Example | Methanol mmol | Methanol equivalents | (±)-2-Azabicyclo[2.2.1]-hept-5-en-3-one % yield | Aminoalcohol % yield |
|---|---|---|---|---|
| 1.8.1 | 9.2 | 1 | 27.5 | 44.8 |
| 1.8.2 | 18.3 | 2 | 13.1 | 66.8 |
| 1.8.3 | 27.5 | 3 | 24.7 | 54.8 |
| 1.8.4 | 36.6 | 4 | 5.7 | 56.8 |
| 1.8.5 | 45.8 | 5 | 12.0 | 58.3 |
| 1.8.6 | 55.0 | 6 | 7.2 | 33.0 |

1.9 Preparation of (±)-1-amino-4-(hydroxymethyl)-2-cyclopentene with Various Solvents Using the procedure of Example 1.7, the reaction was carried out in a variety of solvents (7.5 ml) and the content was determined. The results are given in Table 3.

TABLE 3

| Example | Solvent X | (±)-2-Azabicyclo-[2.2.1]-hept-5-en-3-one % Yield | Aminoalcohol % Yield |
|---|---|---|---|
| 1.9.1 | dioxane | 13.6 | 79.8 |
| 1.9.2 | diethyl ether | 10.8 | 68.6 |
| 1.9.3 | tetrahydrofuran | 22.4 | 67.6 |
| 1.9.4 | diisopropyl ether | 12.6 | 51.3 |
| 1.9.5 | tert-butyl methyl ether | 10.0 | 71.3 |
| 1.9.6 | monoglyme | 15.5 | 75.3 |
| 1.9.7 | formaldehyde dimethyl acetal | 12.0 | 74.2 |

1.10 Preparation of (±)-1-amino-4-(hydroxymethyl)-2-cyclopentene with Various Additions of $LiBH_4$ Following the procedure of Example 1.7, the reaction was carried out using a variety of $LiBH_4$ concentrations, and the content was determined. The results are given in Table 4.

TABLE 4

| Example | $LiBH_4$ mmol | $LiBH_4$ equivalents | (±)-2-Azabicyclo-[2.2.1]-hept-5-en-3-one % yield | Aminoalcohol % yield |
|---|---|---|---|---|
| 1.10.1 | 4.6 | 1 | 11.9 | 47.9 |
| 1.10.2 | 6.9 | 1.5 | 9.6 | 45.6 |
| 1.10.3 | 9.2 | 2 | 12.7 | 71.3 |
| 1.10.4 | 11.5 | 2.5 | 13.3 | 74.5 |
| 1.10.5 | 13.8 | 3 | 12.8 | 77.1 |
| 1.10.6 | 16.1 | 3.5 | 12.7 | 62.4 |

1.11 Preparation (1R, 4S)- and (1S, 4R)-1-amino-4-(hydroxymethyl)-2-cyclopentene in the Presence of Various Alcohols and in the Presence of Water in a Variety of Solvents A 10 ml round-bottom flask fitted with magnetic stirrer was charged with 0.50 g (4.6 mmol) of (±)-2-azabicyclo[2.2.1]hept-5-en-3-one and 0.30 g (13.7 mmol) of lithium borohydride in 6 ml of a variety of solvents, and the mixture was heated to 60° C. At this temperature, over the course of 30 min, 34.3 mmol of the additive Y were added dropwise using a syringe. The mixture was then stirred for 2 h at 60° C., cooled to about 20° C. and poured onto about 10 ml of semi-condentrated HCl.

The content is determined directly using a quantitative ion-chromatographic method (cf. Table 5). The ee value of the product was determined by means of HPLC. The results are given Table 5.

TABLE 5

| Example | (−)-2-Azabicyclo-[2.2.1]hept-5-en-3-one ee value | (+)-2-Azabicyclo-[2.2.1]hept-5-en-3-one ee value | Solvent | Additive Y | Aminoalcohol Yield (IC) | Aminoalcohol ee value (HPLC) |
|---|---|---|---|---|---|---|
| 1 | 98.0 | | dioxane | water | 64.3 | >99.0 |
| 2 | 98.0 | | glyme | water | 68.0 | >99.0 |
| 3 | 75.9 | | dioxane | water | 65.1 | 76.0 |
| 4 | 75.9 | | glyme | water | 63.5 | 75.6 |
| 5 | 50.2 | | dioxane | water | 74.8 | 51.4 |
| 6 | 51.6 | | glyme | water | 64.1 | 53.0 |
| 7 | 25.3 | | dioxane | water | 61.1 | 30.4 |
| 8 | 25.6 | | glyme | water | 61.0 | 29.6 |
| 9 | 98.0 | | dioxane | methanol | 83.1 | 98.2 |
| 10 | 98.0 | | glyme | methanol | 81.5 | 99.2 |
| 11 | 75.9 | | dioxane | methanol | 81.4 | 78.0 |
| 12 | 76.2 | | glyme | methanol | 79.9 | 78.6 |
| 13 | 50.4 | | dioxane | methanol | 81.3 | 54.4 |
| 14 | 51.5 | | glyme | methanol | 82.0 | 55.2 |
| 15 | 24.8 | | dioxane | methanol | 65.2 | 27.4 |
| 16 | 27.8 | | glyme | methanol | 81.7 | 32.2 |
| 17 | 98.0 | | dioxane | ethanol | 80.8 | 80.8 |
| 18 | 98.0 | | glyme | ethanol | 85.1 | 85.1 |
| 19 | 75.5 | | dioxane | ethanol | 85.3 | 78.2 |
| 20 | 75.6 | | glyme | ethanol | 83.6 | 78.4 |
| 21 | 50.7 | | dioxane | ethanol | 76.3 | 54.4 |
| 22 | 51.1 | | glyme | ethanol | 71.3 | 55.2 |
| 23 | 25.4 | | dioxane | ethanol | 73.0 | 28.6 |
| 24 | 25.5 | | glyme | ethanol | 75.0 | 28.6 |
| 25 | | 98.0 | dioxane | water | 62.0 | >99.0 |
| 26 | | 98.0 | glyme | water | 59.5 | >99.0 |
| 27 | | 51.3 | dioxane | water | 79.0 | 52.2 |
| 28 | | 49.0 | glyme | water | 61.3 | 52.0 |
| 29 | | 98.0 | dioxane | methanol | 77.2 | >99.0 |
| 30 | | 98.0 | glyme | methanol | 80.0 | >99.0 |
| 31 | | 49.0 | dioxane | methanol | 80.8 | 46.8 |
| 32 | | 49.5 | glyme | methanol | 80.9 | 48.8 |

1.12 Preparation of (±)-1-amino-4-(hydroxymethyl)-2-cyclopentene Using Sodium borohydride in Various Alcohols Following the procedure of Example 1.7, the reaction was carried out in a variety of alcohols. In contrast to Example 1.7, however, sodium borohydride (0.51 g, 13.7 mmol) was used as reducing agent. The results are given in Table 6.

TABLE 6

| Example | Additive Y | X mmol | X equivalents | (±)-2-Azabicyclo-[2.2.1]-hept-5-en-3-one Yield % | Aminoalcohol y |
|---|---|---|---|---|---|
| 1.12.1 | water | 17.1 | 1.25 | 75.4 | 20.1 |
| 1.12.2 | water | 34.3 | 2.5 | 71.9 | 26.7 |
| 1.12.3 | methanol | 34.3 | 2.5 | 39.2 | 22.2 |
| 1.12.4 | ethanol | 34.3 | 2.5 | 67.8 | 8.6 |
| 1.12.5 | — | — | — | 62.2 | 3.5 |

1.13 Preparation of (±)-1-amino-4-(hydroxymethyl)-2-cyclopentene Using NaBH$_3$CN 60 ml of dioxane and 8.6 g (137 mmol) of sodium cyanoborohydride and 11.9 g (137 mmol) of lithium bromide were refluxed overnight for 15 h at 110° C. in a 100 ml sulphonation flask. The mixture was then cooled to 60° C., and a solution of 5.0 g (45.8 mmol) of (±)-2-azabicyclo[2.2.1]hept-5-en-3-one containing 15 ml of methanol were added dropwise over the course of 30 min. The white suspension was stirred for 3 h at 60° C., cooled to about 5° C. and poured into about 100 ml of semi-concentrated HCl. The content was then determined directly using a quantitative ion-chromatographic method. The yield of amino-alcohol was about 4%.

Example 2

Alkaline Hydrolysis of acetyl-(+)-1-amino-4-(hydroxy-methyl)-2-cyclopentene 88.9 g of racemic acetyl-1-amino-4-(hydroxymethyl)-2-cyclopentene (content 77.2%) were suspended (partially dissolved) in 70 g of water. 84 g of 30% NaOH (1.1 equivalents) were added thereto, and the solution was refluxed for 3 h. According to TLC, the hydrolysis was complete. The resulting acetate was removed by electrodialysis. The obtained aqueous solution was reduced by evaporation and dried by azeotropic distillation with butanol. The residue was taken up in methanol for racemate resolution. Yield of hydrolysis to (±)-1-amino-4-(hydroxymethyl)-2-cyclopentene was 90%.

Example 3

Preparation of (1R, 4S)- or (1S, 4R)-1-amino-4-(hydroxymethyl)-2-cyclopentene 3.1 Racemate Resolution Using Hydrolases 3.1.1 Preparation of (1R, 4S)-1-amino-4-(hydroxymethyl)-2-cyclopentene Using Lipases 3.1.1.1 25 mM of racemic 1-amino-4-(hydroxymethyl)-2-cyclopentene were suspended with 1000 units of Novozym 435 in 5 ml of dioxane at room temperature. 25 mM of ethyl methoxyacetate were added as acetylating agent. The formation of N-methoxyacetylaminoalcohol was unambiguously detected by TLC. The conversion was 50% (according to estimation of the TLC) . This reaction produced (1R, 4S)-1-amino-4-(hydroxymethyl)-2-cyclopentene.

3.1.1.2 50 mM of racemic 1-amino-4-(hydroxymethyl)-2-cyclopentene were suspended with 1000 units (U) of Novozym 435 in 5 ml of tetrahydrofuran. 50 mM of NaOH and 50 mM of ethyl methoxyacetate were added, and the mixture was incubated at 30° C. N-Methoxyacetylaminoalcohol was detected using TLC. The estimated conversion was 50%. This reaction produced (1R, 4S)-1-amino-4-(hydroxymethyl)-2-cyclopentene.

3.1.1.3 11 mg of racemic cis-1-amino-4-(hydroxymethyl)-2-cyclopentene were stirred with 1 ml of methyl tert-butyl ether, 0.06 ml of tributyrin (glyceryl tributyrate) and 20 U of Novozym 435 (immob. lipase from *Candida antarctica*) at room temperature. After 3 days, enantiomerically pure, according to HPLC, (1R, 4S)-1-amino-4-(hydroxymethyl)-2-cyclopentene was obtained in 43% yield.

3.1.1.4 11 mg of racemic cis-1-amino-4-(hydroxymethyl)-2-cyclopentene were stirred with 1 ml of methyl tert-butyl ether. 0.02 ml of 6-caprolactone and 20 U of Novozym 435 (immob. lipase from *Candida antarctica*) at room temperature. After 4 days, (1R, 4S)-1-amino-4-(hydroxymethyl)-2-cyclo-pentene with 87% ee was obtained in 49% yield (HPLC).

3.1.1.5 100 mg of racemic cis-1-amino-4-(hydroxy-methyl)-2-cyclopentene were stirred with 1 ml of hexane, 0.3 ml of tributyrin and 20 U of Novozym 435 (immob. lipase from *Candida antarctica*) at room temperature. After 1 week, (1R, 4S)-1-amino-4-(hydroxymethyl)-2-cyclopentene with 77% ee was obtained in 28% yield (HPLC).

3.1.1.6 100 mg of racemic cis-1-amino-4-(hydroxymethyl)-2-cyclopentene were stirred with 1 ml of tert-butanol, 0.3 ml of tributyrin and 20 U of Novozym 435 (immob. lipase from *Candida antarctica*) at 30° C. After 1 week, (1R, 4S)-1-amino-4- (hydroxymethyl)-2-cyclopentene with 78% ee was obtained in 15% yield (HPLC).

3.1.1.7 11 mg of racemic cis-1-amino-4-(hydroxymethyl)-2-cyclopentene were stirred with 1 ml of methyl tert-butyl ether, 0.2 mmol of methyl caproate and 20 U of Novozym 435 (immob. lipase from *Candida antarctica*) at room temperature. After 4 days (1R, 4S)-1-amino-4-(hydroxymethyl)-2-cyclopentene with 68% ee was obtained in 52% yield (HPLC).

3.1.1.8 11 mg of racemic cis-1-amino-4-(hydroxymethyl)-2-cyclopentene were stirred with 1 ml of methyl tert-butyl ether, 0.2 mmol of glycol dibutyrate and 40 U of Novozym 435 (immob. lipase from *Candida antarctica*) at room temperature. After 4 days, (1R, 4S)-1-amino-4-(hydroxymethyl)-2-cyclopentene with 89% ee was obtained in 31% yield (HPLC).

3.1.1.9 11 mg of racemic cis-1-amino-4-(hydroxymethyl)-2-cyclopentene were stirred with 1 ml of methyl tert-butyl ether, 0.2 mmol of diethyl fumarate and 40 U of Novozym 435 (immob. lipase from *Candida antarctica*) at room temperature. After 4 days, (1R, 4S)-1-amino-4-(hydroxymethyl)-2-cyclopentene with 86% ee was obtained in 36% yield (HPLC).

3.1.1.10 11 mg of racemic cis-1-amino-4-(hydroxymethyl)-2-cyclopentene were stirred with 1 ml of methyl tert-butyl ether, 0.2 mmol of diethyl malonate and 40 U of Novozym 435 (immob. lipase from *Candida antarctica*) at room temperature. After 4 days, (1R, 4S)-1-amino-4-(hydroxymethyl)-2-cyclopentene with 86% ee was obtained in 21% yield (HPLC).

3.1.1.11 11 mg of racemic cis-1-amino-4-(hydroxymethyl)-2-cyclopentene were stirred with 1 ml of diisopropyl ether, 0.2 mmol of tributyrin and 40 U of Novozym 435 (immob. lipase from *Candida antarctica*) at room temperature. After 4 days, enantiomerically pure (1R, 4S)-1-amino-4-(hydroxymethyl)-2-cyclopentene was obtained in 15% yield (HPLC).

3.1.1.12 11 mg of racemic cis-1-amino-4-(hydroxymethyl)-2-cyclopentene were stirred with 1 ml of diisopropyl ether, 0.2 mmol of diethyl fumarate and 40 U of Novozym 435 (immob. lipase from *Candida antarctica*) at room temperature. After 4 days, (1R, 4S)-1-amino-4-(hydroxymethyl)-2-cyclopentene with 88% ee was obtained in 24% yield (HPLC).

3.1.1.13 11 mg of racemic cis-1-amino-4-(hydroxymethyl)-2-cyclopentene were stirred with 1 ml of diisopropyl ether, 0.2 mmol of diethyl malonate and 40 U of Novozym 435 (immob. lipase from *Candida antarctica*) at room temperature. After 4 days, (1R, 4S)-1-amino-4-(hydroxymethyl)-2-cyclopentene with 82% ee was obtained in 14% yield (HPLC).

3.1.1.14 11 mg of racemic cis-1-amino-4-(hydroxymethyl)-2-cyclopentene were stirred with 1 ml of diisopropyl ether, 0.2 mmol of diethyl diglycolate and 40 U of Novozym 435 (immob. lipase from *Candida antarctica*) at room temperature. After 4 days, (1R, 4S)-1-amino-4-(hydroxymethyl)-2-cyclopentene with 88% ee was obtained in 7% yield (HPLC).

3.1.1.15 11 mg of racemic cis-1-amino-4-(hydroxymethyl)-2-cyclopentene were stirred with 1 ml of dibutyl ether, 0.2 mmol of tributyrin and 40 U of Novozym 435 (immobilized lipase from *Candida antarctica*) at room temperature. After 4 days, (1R, 4S)-1-amino-4-(hydroxymethyl)-2-cyclopentene with 95% ee was obtained in 13% yield (HPLC).

3.1.1.16 11 mg of racemic cis-1-amino-4-(hydroxymethyl)-2-cyclopentene were stirred with 1 ml of pyridine, 0.02 ml of ethyl 2-methoxyacetate and 20 mg of lipase AK (lipase from *Pseudomonas fluorescens*) at room temperature. After 4 days, (1R, 4S)-1-amino-4-(hydroxymethyl)-2-cyclopentene with 84% ee was obtained in 18% yield (HPLC).

3.1.1.17 11 mg of racemic cis-1-amino-4-(hydroxymethyl)-2-cyclopentene were stirred with 1 ml of methyl tert-butyl ether, 0.2 mmol of ethyl cyano-acetate and 10 mg of lipase PS (lipase from *Pseudomonas cepacia*) at room temperature. After 4 days, (1R, 4S)-1-amino-4-(hydroxymethyl)-2-cyclopentene with 67% ee was obtained in 40% yield (HPLC).

3.1.1.18 11 mg of racemic cis-1-amino-4-(hydroxymethyl)-2-cyclopentene were stirred with 1 ml of methyl tert-butyl ether, 0.2 mmol of diethyl fumarate and 10 mg of lipase PS (lipase from *Pseudomonas cepacia*) at room temperature. After 4 days, (1R, 4S)-1-amino-4-(hydroxymethyl)-2-cyclopentene with 86% ee was obtained in 18% yield (HPLC).

3.1.2 Preparation of (1R, 4S)-1-amino-4-(hydroxymethyl)-2-cyclopentene Using Proteases 3.1.2.1 11 mg of racemic cis-1-amino-4-(hydroxymethyl)-2-cyclopentene were stirred with 1 ml of 2-methyl-2-butanol, 0.2 mmol of diethyl maleate and 40 mg of Alcalase (protease from *Bacillus licheniformis*) at room temperature. After 4 days, (1R, 4S)-1-amino-4-(hydroxymethyl)-2-cyclopentene with 28% ee was obtained in 39% yield (HPLC).

3.1.2.2 11 mg of racemic cis-1-amino-4-(hydroxymethyl)-2-cyclopentene were stirred with 1 ml of 2-methyl-2-butanol, 0.2 mmol of diethyl fumarate and 40 mg of Savinase (protease from *Bacillus* sp.) at room temperature. After 4 days, (1R, 4S)-1-amino-4-(hydroxymethyl)-2-cyclopentene with 32% ee was obtained in 42% yield (HPLC).

3.1.2.3 11 mg of racemic cis-1-amino-4-(hydroxymethyl)-2-cyclopentene were stirred with 1 ml of 2-methyl-2-butanol, 0.06 ml of tributyrin and 20 mg of Savinase (protease from *Bacillus* sp.) at room temperature. After 4 days, (1R, 4S)-1-amino-4-(hydroxymethyl)-2-cyclopentene with 22% ee was obtained in 39% yield (HPLC).

3.1.2.4 11 mg of racemic cis-1-amino-4-(hydroxymethyl)-2-cyclopentene were stirred with 1 ml of 2-methyl-2-butanol, 0.06 ml of tributyrin and 20 mg of subtilisin (protease from *Bacillus licheniformis*) at room temperature. After 4 days, (1R, 4S)-1-amino-4-(hydroxymethyl)-2-cyclopentene with 23% ee was obtained in 36% yield (HPLC).

3.1.3 Preparation of (1S, 4R)-1-amino-4-(hydroxymethyl)-2-cyclopentene Using Proteases 3.1.3.1 11 mg of racemic cis-1-amino-4-(hydroxymethyl)-2-cyclopentene were stirred with 1 ml of hexane, 0.06 ml of tributyrin and 120 U of Savinase (protease from *Bacillus* sp.) at room temperature. After 3-6 days, (1S, 4R)-1-amino-4-(hydroxymethyl)-2-cyclopentene with 44% ee was obtained in 46% yield (HPLC).

3.1.3.2 11 mg of racemic cis-1-amino-4-(hydroxymethyl)-2-cyclopentene were stirred with 1 ml of hexane, 0.06 ml of tributyrin and 20 mg of Alcalase (protease from *Bacillus licheniformis*) at room temperature. After 3-6 days, (1S, 4R)-1-amino-4-(hydroxymethyl)-2-cyclopentene with 44% ee was obtained in 35% yield (HPLC).

3.1.4 Preparation of (1S, 4R)-1-amino-4-(hydroxymethyl)-2-cyclopentene Using Lipases 3.1.4.1 11 mg of racemic cis-1-amino-4-(hydroxymethyl)-2-cyclopentene were stirred with 1 ml of 2-methyl-2-butanol, 0.03 ml of ethyl butyrate and 20 mg of Newlase F (lipase from *Rhizopus niveus*) at room temperature. After 1 week, (1S, 4R)-1-amino-4-(hydroxymethyl)-2-cyclopentene with 39% ee was obtained in 37% yield (HPLC).

3.1.4.2 11 mg of racemic cis-1-amino-4-(hydroxymethyl)-2-cyclopentene were stirred with 1 ml of pyridine, 0.06 ml of tributyrin and 20 mg of lipase AK (lipase from *Pseudomonas fluorescens*) at room temperature. After 1 week, (1S, 4R)-1-amino-4-(hydroxymethyl)-2-cyclopentene with 30 % ee was obtained in 10% yield (HPLC).

3.1.4.3 11 mg of racemic cis-1-amino-4-(hydroxymethyl)-2-cyclopentene were stirred with 1 ml of 2-methyl-2-butanol, 0.06 ml of tributyrin and 20 mg of lipase AY (lipase from *Candida rugosa*) at room temperature. After 1 week, (1S, 4R)-1-amino-4-(hydroxymethyl)-2-cyclopentene with 32% ee was obtained in 13% yield (HPLC).

3.1.4.4 11 mg of racemic cis-1-amino-4-(hydroxymethyl)-2-cyclopentene were stirred with 1 ml of methyl t-butyl ether, 0.06 ml of tributyrin and 20 mg of lipase PS-CL (immobilized lipase from *Pseudomonas cepacia*) at room temperature. After 1 week, (1S, 4R)-1-amino-4-(hydroxymethyl)-2-cyclopentene with 29% ee was obtained in 16% yield (HPLC).

3.1.4.5 11 mg of racemic cis-1-amino-4-(hydroxymethyl)-2-cyclopentene were stirred with 1 ml of methyl t-butyl ether, 0.06 ml of tributyrin and 20 mg of lipase PS (lipase from *Pseudomonas cepacia*) at room temperature. After 1 week, (1S, 4R)-1-amino-4-(hydroxymethyl)-2-cyclopentene with 24% ee was obtained in 22% yield (HPLC).

3.2 Racemate Resolution Using D-(−)-Tartaric Acid 3.2.1 A mixture of 8 g (70.6 mmol) of racemic 1-amino-4-(hydroxymethyl)-2-cyclopentene and 10.6 g (70.6 mmol) of D-(−)-tartaric acid in 186 g of methanol were dissolved at the reflux temperature. The mixture was then cooled to 20° C. over 2 h. At 43° C., seed crystals of the pure (1R, 4S)-1-amino-4-(hydroxymethyl)-2-cyclopentene D-hydrogentartrate were added. The crystallized product was filtered off and dried. Yield: 8.49 g (45.6% based on racemic starting material) of (1R, 4S)-1-amino-4-(hydroxymethyl)-2-cyclopentene D-hydrogentartrate, ee value: 91.1%. For purification, 8.49 g (32.25 mmol) of the hydrogentartrate were suspended in 30 ml of methanol, and 2 equivalents of 30% sodium methoxide were added. The sodium tartrate was filtered off and the methanol was distilled off.

The residue was taken up in 35 ml of pentanol. Then, at 55° C., 1.5 g of HCl were introduced, and the solution was slowly cooled. At 40° C., the solution was seeded with (1R, 4S)-1-amino-4-(hydroxymethyl)-2-cyclopentene hydrochloride. 45 ml of acetone were then metered in, and the suspension was slowly cooled to 0° C. and filtered, and the residue was dried. 3.91 g of (1R, 4S)-1-amino-4-(hydroxymethyl)-2-cyclopentene hydrochloride having an ee value of >98% were obtained, corresponding to a yield, based on racemic (1R, 4S)-1-amino-4-(hydroxymethyl)-2-cyclopentene used, of 37%.

3.2.2 A mixture of 64 g of racemic 1-amino-4-(hydroxymethyl)-2-cyclopentene (0.5 mol) and 75.2 g of D-(−)-tartaric acid in 1330 g of methanol was dissolved at the reflux temperature and then cooled to 20° C. over 2 h. At 430° C., seed crystals of the pure 1R, 4S-enantiomer were added. The crystallized product was filtered off and dried. Yield: 63.2 g (48.0% based on racemic 1-amino-4-(hydroxymethyl)-2-cyclopentene) of (1R, 4S)-1-amino-4-(hydroxymethyl)-2-cyclopentene hydrogentartrate, ee value: 91.1%. The ee value in the mother liquor was 76.0%.

3.2.3 Recrystallization of 1R, 4S-(4-amino-2-cyclopenten-1-yl)methanol D-hydrogentartrate 61.84 g of 1R, 4S-(4-amino-2-cyclopenten-1-yl)-methanol D-hydrogentartrate (0.235 mol, ee value 91.1%) were dissolved in 752 g of methanol under reflux. The solution was cooled to 20° C. within 90 min, then the product was filtered off and washed with 64 g of cold methanol. Drying gave 54.56 g of 1R, 4S-(4-amino-2-cyclopenten-1-yl)-methanol D-hydrogentartrate were obtained, ee value 99.4% (yield 88.2%, 42.3% based on racemic 1-amino-4-(hydroxymethyl)-2-cyclopentene). This was used tel quel in the chloropurine synthesis.

3.2.4 Following the procedure of Example 3.2.2, but using 223 g of methanol and seeding at 50° C., the racemate was separated. The yield was 7.98 g (42.9% based on racemic (1R, 4S)-1-amino-4-(hydroxymethyl)-2-cyclopentene used).

3.3 Racemate Resolution Using L-(+)-Tartaric Acid 3.3.1 A mixture of 8 g (70.6 mmol) of racemic 1-amino-4-(hydroxymethyl)-2-cyclopentene and 10.6 g (70.6 mmol) of L-(+)-tartaric acid in 186 g of methanol were dissolved at the reflux temperature. The mixture was then cooled to 20° C. over 2 h. At 43° C., seed crystals of the pure (1S, 4R)-1-amino-4-(hydroxymethyl)-2-cyclopentene L-hydrogentartrate were added. The crystallized (1S, 4R)-1-amino-4-(hydroxymethyl)-2-cyclopentene L-hydrogentartrate was filtered off and dried. (ee value: 91.1%). 14 g of 30% methanolic sodium methoxide were added to the mother liquor, then the methanol was evaporated. The residue was taken up in 35 ml of isobutanol, and the insoluble sodium tartrate was filtered off. At 55° C., 2 g of gaseous HCl were introduced into the filtrate. 38 ml of acetone were then added, and the mixture was left to cool to 10° C. over the course of 1 h. After 1 h, the (1R, 4S)-1-amino-4-(hydroxymethyl)-2-cyclopentene hydrochloride was filtered off with suction and washed with 8 ml of acetone. Drying under reduced pressure gave the (1R, 4S)-1-amino-4-(hydroxymethyl)-2-cyclopentene hydrochloride in a yield of 34 g, 31.6% based on racemic 1-amino-4-(hydroxymethyl)-2-cyclopentene with an ee value of >98%.

Example 4

Preparation of (1R, 4S)-amino-4-(hydroxymethyl)-2-cyclopentene hydrochloride 4.1 Reduction of (−)-2-azabicyclo[2.2.1]hept-5-en-3-one A 2 l autoclave (stainless steel type V4A) rendered inert with $N_2$, was charged with 61.4 g of sodium borohydride 97.5% (1.623 mol), 70.2 g of lithium chloride 98.5% (1.656 mol), 13.2 g of Celite and 1410 g of tetrahydrofuran. The autoclave was closed and heated to an internal temperature of 130° C. and the contents stirred for 4.5 hours at this temperature (max. 8.0 bar).

After the autoclave had been cooled to about 60° C., the sodium salts insoluble in tetrahydrofuran (NaCl, $NaBH_4$) were filtered off. These were washed with 353 g of tetrahydrofuran, and the combined filtrates were reduced to about half in a stirred 1 l glass vessel by distillation at atmospheric pressure (distillate 1: about 710 g of tetrahydrofuran). Further distillation, alternating with the portion-wise addition of a total of 936 g of dioxane then completed the solvent exchange (distillate 2: about 1289 g of tetrahydrofuran/dioxane).

The $LiBH_4$ suspension was cooled to about 60° C., and 56.7 g of (−)-2-azabicyclo[2.2.1hept-5-en-3-one (97.5%) were added.

Starting at about 60° C., 132.5 g of methanol were metered in in exactly one hour at a rate such that a temperature range of 58-62° C. was maintained. The mixture was then allowed to react for a further hour at 60° C. A further 397.0 g of methanol were then added (sample comprises an analytical yield of 70.5%), and the contents of the stirred vessel were cooled to 0° C. At this temperature, 90.0 g of HCl were introduced into the reaction mixture (slightly exothermic) and stirring was continued for a further hour at about 0° C. Distillation at atmospheric pressure (up to a head temperature of 75° C.) removed the low-boiling fractions (methanol, borate) and about 70% of the dioxane (distillate 3: about 1093 g). Distillation under reduced pressure (about 30 mbar), alternating with the portionwise addition of a total of 282 g of 1-pentanol then completed the solvent exchange (distillate 4: about 240 g of dioxane/pentanol).

After a further 302 g of 1-pentanol had been added, the mixture was stirred for 1 hour at 50° C., and precipitated salts, about 39 g moist weight, were filtered off and washed with 200 g of 1-pentanol. The combined filtrates were reduced by redistillation under reduced pressure (about 20 mbar) (distillate 5: 235 g of 1-pentanol). Then, at about 50° C., 236 g of acetone were metered in, and the reaction mixture was seeded with a few crystals of (1R, 4s)-amino-4-(hydroxymethyl)-2-cyclopentene. The mixture was cooled to 5° C. over the course of 1 hour, and crystallization was completed by stirring the mixture for a further 6 h at 5° C.

The crystals were filtered off, washed with 63 g of acetone and dried at a max. 50° C. in a vacuum drying cabinet (10 mbar). This gave 83.5 g of crude product* (content: 56.5%).

This corresponded to a yield of 61.4% based on (−)-2-azabicyclo[2.2.1]hept-5-en-3-one used.

4.2 Reduction of (±)-2-azabicyclo[2.2.1]hept-5-en-3-one

A 2 l autoclave (stainless steel type V4A) rendered inert with $N_2$, was charged with 41.56 g of sodium borohydride 97.5% (1.071 mol), 51.48 g of lithium chloride 98.5% (1.196 mol), 9.30 g of Celite and 955.0 g of tetrahydrofuran. The autoclave was closed and heated to an internal temperature of 130° C. and the contents stirred for 6 hours at this temperature (max. 6.3 bar).

After the autoclave had been cooled to about 60° C., the sodium salts insoluble in tetrahydrofuran (NaCl, $NaBH_4$) were filtered off. These were washed with 239.0 g of tetrahydrofuran, and the combined filtrates were reduced to about half in a stirred 1 l glass vessel by distillation at atmospheric pressure. (distillate 1: about 590 g of THF). Further distillation, alternating with the portionwise addition of a total of 661.0 g of dioxane then completed the solvent exchange (distillate 2: about 685 g of tetrahydrofuran/dioxane).

The $LiBH_4$ suspension was cooled to about 60° C., and 36.0 g of 2-azabicyclo[2.2.1]hept-5-en-3-one (97.5%) were added.

Starting at about 60° C., 77.6 g of methanol were metered in in exactly one hour at a rate such that a temperature range of 58-62° C. was maintained. The mixture was then allowed to react for a further hour at 60° C. A further 233.0 g of methanol were then added, and the contents of the stirred vessel were cooled to 0° C. At this temperature, 52.9 g of HCl were introduced into the reaction mixture (slightly exothermic) and stirring was continued for a further hour at about 0° C. Distillation at atmospheric pressure (up to a head temperature of 75° C.) removed the low-boiling fractions (methanol, borate) and about 70% of the dioxane (distillate 3: about 700 g). Distillation under reduced pressure (about 30 mmol), alternating with the portionwise addition of a total of 169.4 g of 1-pentanol then completed the solvent exchange (distillate 4: about 183 g of dioxane/pentanol). After a further 127.1 g of 1-pentanol had been added, the mixture was stirred for 1 hour at 50° C., and precipitated salts, about 41 g moist weight, were filtered off and washed with 63.5 g of 1-pentanol. The combined filtrates were reduced by redistillation under reduced pressure (about 20 mbar) (distillate 5: 235 g of 1-pentanol) Then, at about 50° C., 238.0 g of acetone were metered in, and the reaction mixture was seeded with a few crystals of aminoalcohol hydrochloride salt. The mixture was cooled to 5° C. over the course of one hour, and crystallization was completed by stirring the mixture for a further 6 hours at 5° C.

The crystals were filtered off, washed with 61.0 g of acetone and dried at a max. 50° C. in a vacuum drying cabinet (10 mbar). This gave 50.0 g of crude product (content: about 50% of aminoalcohol hydrochloride salt).

This corresponded to a yield of 52.0% based on 2-azabicyclo[2.2.1]hept-5-en-3-one used.

Example 5

Preparation of Acylated Aminoalcohols

5.1 Preparation of (1R, 4S)-N-BOC-1-amino-4-(hydroxy-methyl)-2-cyclopentene (BOC=tert-butoxycarbonyl)

75 g of a solution of (1R, 4S)-1-amino-4-hydroxy-methyl-2-cyclopentene were adjusted to pH 8 using 30% strength NaOH, and 6 g of NaHCO$_3$ were added to the mixture. The mixture was heated to 52° C. Whilst stirring the mixture thoroughly, 60 ml of diisopropyl ether were added thereto and then, over the course of 2 h, a solution of 11.12 g of BOC anhydride in 18.2 ml of diisopropyl ether were metered in. The mixture was filtered over Celite, and the phases were separated. The aqueous phase was extracted with 65 ml of diisopropyl ether. The combined organic phases were washed with 45 ml of water, then evaporated to 37.5 g and heated to 50° C. 31 ml of n-hexane were added dropwise to the solution. After the mixture had been slowly cooled to 0° C. (2 h), the title compound was filtered, washed with 12 ml of n-hexane/diisopropyl ether 1/1 and dried. This gave 6.75 g of product. The yield was 71%.

5.2 Preparation of (1R, 4S)-N-acetyl-1-amino-4-(hydroxy-methyl)-2-cyclopentene 25 g (1R, 4s)-1-amino-4-(hydroxymethyl)-2-cyclopentene hydrochloride were dissolved in 182 ml of acetic anhydride, and at 0° C., a solution of 18.25 g of triethylamine in 60 ml of acetic anhydride were added thereto. The mixture was stirred at 80° C. for 3 h, then cooled to room temperature. The triethylamine hydrochloride was filtered off and washed with 120 ml of n-hexane. The filtrate was evaporated. 300 ml of toluene were added to the residue, and the mixture was stirred at room temperature in the presence of 5.2 g of activated carbon and 13 g of Celite for 20 min. The mixture was then filtered, and the filter cake was washed (3×40 ml of toluene), and the solvent was completely evaporated. 180 ml of methanol and 15.5 g of K$_2$CO$_3$ were added to the residue, and the mixture was stirred at room temperature for 10 h. The suspension was filtered off and the filtrate evaporated. The residue was suspended in 750 ml of isopropyl acetate and boiled in the presence of 0.5 g of activated carbon to reflux for 1.5 h. Following filtration of the activated carbon (70-80° C.), the filtrate was cooled at 0° C. overnight. The title compound was filtered, washed with 80 ml of cold isopropyl acetate and dried under reduced pressure to give 17.2 g of product. The yield was 66%.

5.3 Preparation of (1R, 4S)-N-butyryl-1-amino-4-(hydroxymethyl)-2-cyclopentene 34.7 g of (1R, 4s)-1-amino-4-hydroxymethyl-2-cyclopentene hydrochloride and 2 g of N,N-4-dimethyl-aminopyridine were dissolved in 600 ml of methylene chloride. The solution was cooled to 0° C. 52 g of triethylamine were then added dropwise (5 min). The mixture was stirred for a further 30 min. At 0° C., a solution of 35.2 g of butyryl chloride in 60 ml of methylene chloride was metered into the mixture over the course of 1 h. The mixture was stirred for a further 1.5 h at between 0 and 20° C., and then 600 ml of water were added thereto. Following phase separation, the aqueous phase was extracted with 600 ml of methylene chloride. The combined organic phases were washed 3×500 ml of 10% strength NaOH, then completely evaporated. The dried solid was dissolved in 120 ml of methanol. 5 g of K$_2$CO$_3$ were added to the solution, and the mixture was stirred for a further 2 h at room temperature. The inorganic salts were filtered off and washed with 20 ml of methanol. The filtrate was neutralized with 2N HCl. The suspension was filtered off, and the filter cake was washed with 20 ml of methanol. The filtrate was completely evaporated. The solid residue was dried and crystallized in 150 ml of toluene to give 28.5 g of the title compound. The yield was 67%.

Example 6

Preparation of [4(R)-(2-amino-6-chloropurine-9-yl) cyclopent-2-ene-1(S)-yl]methanol

6.1 Preparation of [4(R)-(2-amino-6-chloropurine-9-yl)-cyclopent-2-ene-1(S)-yl]methanol starting from 1R, 4S-(4-amino-2-cyclopenten-1-yl)methanol D-hydrogentartrate 47.4 g of 1R, 4S-(4-amino-2-cyclopenten-1-yl)methanol D-hydrogentartrate (0.18 mol, ee>98%) in 200 ml of ethanol were introduced initially. At room temperature, 54.6 g of NaHCO$_3$ (0.65 mol) and 37.3 g (0.18 mol) of N-(2-amino-4,6-dichloro-4-pyrimidyl)-formamide were added, boiled for 9 h under reflux and then cooled to room temperature. The salts were filtered off and then washed with 50 ml of ethanol. The filtrate was concentrated to 280 g on a rotary evaporator. 18.4 g of HCl gas were introduced into the resulting solution at T<25° C., then 95.5 g (0.9 mol) of trimethyl orthoformate were added, and the whole was heated to 40° C. (10 min). At this temperature, the mixture was seeded with chloropurine hydrochloride. After 2 h at 42° C., the product crystallized out. The suspension was cooled to 15° C. The product was filtered and then washed with 3×50 ml of ethanol, then dried at 50° C. under reduced pressure. The yield was 41.9 g (75.8%). Beige powder, content (HPLC): 95.0%.

6.2 Preparation of [4(R)-(2-amino-6-chloropurine-9-yl)-cyclopent-2-ene-1(S)-yl]methanol starting from (−)-2-azabicyclo[2.2.1]hept-5-en-3-one A 2 l autoclave (stainless steel type V4A) rendered inert with N$_2$, was charged with 61.4 g of sodium borohydride 97.5% (1.623 mol), 70.2 g of lithium chloride 98.5% (1.656 mol), 13.2 g of Celite and 1410 g of tetrahydrofuran. The autoclave was closed and heated to an internal temperature of 130° C. and the contents stirred for 4.5 hours at this temperature (max. 8.0 bar). After the autoclave had been cooled to about 60° C., the sodium salts insoluble in tetrahydrofuran (NaCl, NaBH$_4$) were filtered off. These were washed with 353 g of tetrahydrofuran, and the combined filtrates were reduced to about half in a stirred 1 l glass vessel by distillation at atmospheric pressure (distillate 1: about 710 g of tetrahydrofuran). Further distillation, alternating with the portionwise addition of a total of 936 g of dioxane then completed the solvent exchange (distillate 2: about 1289 g of tetrahydrofuran/dioxane).

The LiBH₄ suspension was cooled to about 60° C., and 56.7 g of (−)-2-azabicyclo(2.2.1]hept-5-en-3-one (97.5%/0.507 mol) were added.

Starting at about 60° C., 132.5 g of methanol were metered in in exactly one hour at a rate such that a temperature range of 58-62° C. was maintained. The mixture was then allowed to react for a further hour at 60° C. A further 397.0 g of methanol were then added (sample comprises an analytical yield of 70.5%), and the contents of the stirred vessel were cooled to 0° C. At this temperature, 90.0 g of HCl were introduced into the reaction mixture (slightly exothermic) and stirring was continued for a further hour at about 0° C. The solution was evaporated on a rotary evaporator at 50° C. under reduced pressure, 200 ml of methanol were added and the methanol was removed again (filtration with suction of the methyl borate). The procedure was repeated using a further 200 ml of methanol. 250 ml of ethanol were added to the oil obtained (253.4 g comprise 3.16% of amino-alcohol; this corresponded to 0.360 mol), and the mixture was poured into a 1 l double-jacketed stirred vessel. At room temperature, 72.6 g of NaHCO₃ (0.86 mol) and 74.6 g (0.360 mol) of N-(2-amino-4,6-dichloro-4-pyrimidyl)formamide were added, the mixture was refluxed for 9 h and cooled to room temperature, and the salts were filtered off and then washed with 100 ml of ethanol. The filtrate on the rotary evaporator was concentrated to 560 g. 63.4 g of HCl gas were introduced into the resulting solution at T<25° C., then 191.0 g (1.80 mol) of trimethyl orthoformate were added, and the mixture was heated to 40° C. (10 min). At this temperature, the mixture was seeded with chloropurine hydrochloride, and left to crystallize for 2 h at 42° C. The suspension was cooled to 15° C. The product was filtered and then washed with 3×50 ml of ethanol, then dried at 50° C. under reduced pressure. The yield was 66.0 g (59.7%). Beige powder, content (HPLC): 89.3%. This corresponded to a yield of 42.4% based on the Vince lactam used.

The invention claimed is:

1. A process for preparing (1S, 4R)- or (1R,4S)-1-amino-4-(hydroxymethyl)-2-cyclopentene of the formula:

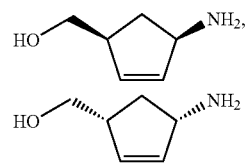

or a salt thereof or a (1S,4R)- or (1R,4S)-1-amino-4-(hydroxymethyl)-2-cyclopentene derivative of the general formula:

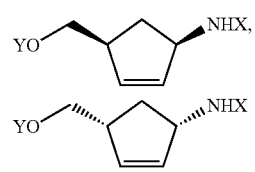

or a salt thereof, in which X and Y are identical or different providing that X and Y are an acyl group or H, with the exception of X=Y=H, comprising resolving the racemate of the formula:

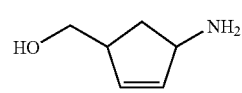

either into its separate enantiomers by using a hydrolase.

2. The process according to claim 1, characterized in that the hydrolase is a lipase.

* * * * *